United States Patent [19]

Kamegai et al.

[11] Patent Number: 5,372,744
[45] Date of Patent: Dec. 13, 1994

[54] DETERGENT COMPOSITION

[75] Inventors: Jun Kamegai, Ichikawa; Hiromi Takamura; Hajime Hirota, both of Tokyo, Japan

[73] Assignee: Kao Corporation, Tokyo, Japan

[21] Appl. No.: 178,435

[22] Filed: Jan. 6, 1994

Related U.S. Application Data

[63] Continuation of Ser. No. 825,834, Jan. 28, 1992, abandoned, which is a continuation of Ser. No. 548,859, Jul. 6, 1990, abandoned.

[30] Foreign Application Priority Data

Jul. 19, 1989 [JP] Japan .................. 1-187016

[51] Int. Cl.$^5$ .................. C11D 1/722; C11D 1/02
[52] U.S. Cl. .................. 252/174.17; 252/DIG. 1; 252/DIG. 13; 252/DIG. 14; 252/DIG. 5; 252/106; 252/174.13; 424/70.13; 424/70.21; 424/70.22
[58] Field of Search .................. 252/174.17, DIG. 13, 252/DIG. 14, DIG. 1, DIG. 5; 424/70, 71

[56] References Cited

U.S. PATENT DOCUMENTS

| | | | |
|---|---|---|---|
| 4,374,056 | 2/1983 | Watanabe et al. | 252/546 |
| 4,479,893 | 10/1984 | Hirota et al. | 252/542 |
| 4,663,069 | 5/1987 | Llenado | 252/117 |
| 4,668,422 | 5/1987 | Malik et al. | 252/174.17 |
| 4,786,494 | 11/1988 | Hirota et al. | 424/70 |
| 4,919,846 | 4/1990 | Nakama et al. | 252/542 |
| 5,015,414 | 5/1991 | Kamegai et al. | 252/545 |
| 5,057,311 | 10/1991 | Kamegai et al. | 424/70 |
| 5,062,989 | 11/1991 | Kamegai et al. | 252/174.17 |
| 5,120,464 | 6/1992 | Kamegai et al. | 252/174.17 |

FOREIGN PATENT DOCUMENTS

| | | |
|---|---|---|
| 070074 | 1/1983 | European Pat. Off. . |
| 2421605 | 12/1979 | France . |
| 6469695 | 3/1989 | Japan . |
| 8000452 | 3/1980 | WIPO . |

OTHER PUBLICATIONS

Derwent Abstract 86-032051, May 1986.

*Primary Examiner*—Paul Lieberman
*Assistant Examiner*—Kery A. Fries
*Attorney, Agent, or Firm*—Oblon, Spivak, McClelland, Maier & Neustadt

[57] ABSTRACT

A low-irritant detergent composition comprising (A) an alkyl saccharide surfactant and (B) a sucrose fatty acid ester surfactant, and, optionally, (C) an anionic surfactant or amphoteric surfactant is disclosed. The composition is low-irritant to the skin and hair and produces creamy and abundant foam, giving an excellent slippery feel to the skin and the hair.

8 Claims, No Drawings

DETERGENT COMPOSITION

This application is a continuation of application Ser. No. 07/825,834, filed on Jan. 28, 1992, now abandoned, which is a continuation of application Ser. No. 07/548,859 filed Jul. 6, 1990, abandoned.

BACKGROUND OF THE INVENTION

1. Field of the Invention

This invention relates to a detergent composition having good foaming capability suitable for shampoos, body shampoos, and the like, and, more particularly, to a low-irritant detergent composition comprising an alkyi saccharide surfactant and a sucrose fatty acid ester, and, optionally, an anionic surfactant and/or an amphoteric surfactant. The composition is low-irritant to the skin and hair, producing excellent creamy foam.

2. Description of the Background Art

Nonionic surfactants have widely been used in detergent compositions for washing the skin and hair. Although nonionic surfactants possess an advantage of being less irritating, their foaming capability is inadequate for detergent compositions requiring good foaming capability, such as hair shampoos, body shampoos, and the like. Therefore, a large amount of nonionic surfactants could not be formulated into such detergent compositions.

Among nonionic surfactants, alkyl saccharide surfactants are known as having comparatively good foaming capability and used as a component of detergent compositions requiring high foaming capability (European Patent No. 70,074 and U.S. Pat. No. 3,219,656).

However, the use of a large amount of alkyl saccharide surfactants have a disadvantage of producing coarse and non-creamy foam when incorporated in a shampoo or a body shampoo which requires creamy foam.

Therefore, the development of a detergent composition exhibiting low irritation to the skin and hair and producing excellent creamy foam has greatly been demanded.

In view of this situation, the present inventors have undertaken extensive studies, and have found that a detergent composition comprising an alkyl sacchariae surfactant and a sucrose fatty acid ester, and, as required, an anionic surfactant and/or an amphoteric surfactant produced fine and creamy foam suitable for shampoos and body shampoos and, at the same time, was only slightly irritant to the skin and the hair.

SUMMARY OF THE INVENTION

Accordingly, an object of this invention is to provide a detergent composition comprising:

(A) 0.1 to 50% by weight of an alkyl saccharide surfactant;

(B) 0.1 to 20% by weight of a sucrose fatty acid ester; and (C) 0 to 30% by weight of at least one anionic surfactant, or at least one amphoteric surfactant, or both.

Other objects, features and advantages of the invention will hereinafter become more readily apparent from the following description.

DETAILED DESCRIPTION OF THE INVENTION AND PREFERRED EMBODIMENTS

As alkyl saccharide surfactants, component (A) of this invention, those represented by formula (I) are preferable,

$$R_1-O-(R_2O)_m-(G)_n \qquad (I)$$

wherein $R_1$ represents a linear or branched alkyl, alkenyl, or alkylphenyl group having $C_{6-18}$ carbon atoms, $R_2$ represents an alkylene group having $C_{2-4}$ carbon atoms, G represents a reducing sugar of a $C_{5-6}$ carbon atom content, m denotes a value of 0 to 10, and n denotes a value of 1 to 10.

For $R_1$ in formula (I), among linear or branched alkyl, alkenyl, or alkylphenyl groups of a $C_{6-18}$ carbon atom content, linear or branched alkyl groups of a $C_{10-14}$ carbon atom content such as decyl-, lauryl-, myristyl group are particularly preferable. The value of m in formula (I) can be 0 to 10, but is preferably from 0 to 3. The basic unit of the saccharide portion, i.e., G in formula (I) which is the hydrophilic group of the alkyl saccharide surfactant, is a reducing sugar having $C_{5-6}$ carbon atoms. Glucose, galactose, and fructose are named as examples of desirable reducing sugars. The degree of polymerization of saccharide (S), i.e., the value of n in formula (I), is 1 to 10. In particular, the use of alkyl saccharide surfactants containing 80% or more of saccharide portion having the degree of polymerization (S) of 1 to 4 is desirable. When the influence of both the polymerization (S) and the group $R_1$ on the compound (I) are taken into account, the desirable value of (S) is 1 to 1.4 when the $R_1$ group is $C_{8-11}$, and 1.5 to 4.0 when the $R_1$ group is $C_{12-14}$. The mean value of (S) is determined by the proton-NMR method.

Given as specific examples of alkyl saccharide surfactants are those synthesized by the Koenings-Knorr method such as octylglucoside, dodecylmaltoside, decylglucoside, polyoxyethylene(3 E.O.)dodecylglucoside, and the like. Included also as these alkyl saccharide surfactants are those synthesized from a reducing sugar such as glucose, galactose, maltose, fructose, or the like and a linear or branched higher alcohol having $C_{6-18}$ atoms such as decanol, or an ethylene oxide or propylene oxide adduct of linear or branched higher alcohol having $C_{6-18}$ carbon atoms such as polyoxyethylene(3 E.O.)dodecylether, or the like (U.S. Pat. Nos. 3,219,656, 3,839,318, and 4,223,129).

Component (A) is formulated into the detergent composition of this invention in an amount of 0.1 to 50% by weight, preferably 1 to 40% by weight.

Sucrose fatty acid esters, component (B) of the present invention, are for example, those represented by the following formula (II):

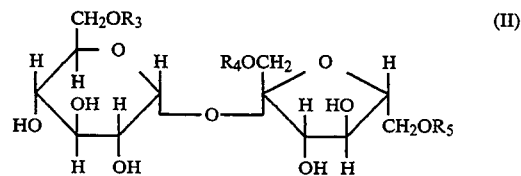

wherein $R_3$, $R_4$, and $R_5$, which may be the same or different, represents a linear or branched, saturated or unsaturated acyl group of a $C_{8-24}$ carbon atom content or a hydrogen atom, provided that at least one of $R_3$, $R_4$, or $R_5$ is the acyl group. This type of sucrose fatty acid esters are usually available as a mixture of mono-, di-, and tri-acyl compounds. Preferable groups for $R_3$, $R_4$, and $R_5$, which may represent acyl groups of a $C_{6-24}$ carbon atom content, are those of a $C_{10-18}$ atom content. The proportion of mono-/di-or tri-acyl compounds is preferably in a range of 70/30 to 30/70.

Component (B) is incorporated in a detergent composition in an amount of 0.1 to 20% by weight, preferably 0.3 to 10% by weight.

As anionic surfactants or amphoteric surfactants used as component (C) of the present invention, any known anionic or amphoteric surfactants can be used. Preferable examples of the anionic surfactant are those having an anionic group selected from sulfate, sulfonate, carboxylate, and phosphate, or a mixture of them. Given as examples of sulfate or sulfonate-type surfactants are alkyl sulfate, polyoxyethylene alkyl sulfate, sulfosuccinate-type, taurate-type, isethionate-type, α-olefin sulfonate-type, and the like. As examples of carboxylate-type surfactants, fatty acid salt, ether carboxylate-type, amino acid-type are given. Examples of phosphate-type surfactants are alkyl phosphates and the like. Among these surfactants, sulfosuccinate-type and phosphate-type surfactants are preferably used.

Examples of the amphoteric surfactant are carbobetaine-type, sulfobetaine-type, imidazolinium betaine-type, and the like. Among them, 2-hydroxypropyl sulfobetaine, desalted secondary imidazolinium betaine disclosed in Japanese Patent Laid-open No. 130129/1988, and the like are preferably used.

One or more of these anionic and amphoteric surfactants can be used in combination as component (C) of the present invention. Component (C) is formulated in the detergent composition in an amount of 0 to 30% by weight, preferably 5 to 20% by weight.

Besides the above-described essential components, other components which are generally used in detergent compositions may be optionally formulated into the composition of the present invention inasmuch as the effect of the present invention is not adversely affected. Such components include, for example, humectants such as propylene glycol, glycerin, sorbitol, and the like; viscosity adjusting agents such as methyl cellulose, polyoxyethyleneglycol distearate, ethanol, and the like; biocidal agents such as Trichlosan, Trichlorocarban, and the like; antiphlogistic agents such as potassium glycyrrhetinate, tocopherol acetate, and the like; antidandruff agents such as zinc pyrithione, octopirox, and the like; antiseptics such as methyl paraben, butyl paraben, and the like; pearlescent agents; perfumes; pigments; ultraviolet ray absorbers; antioxidants; and the like.

The detergent composition of this invention can be provided in any preparation forms conventionally employed. The desirable proportion of the components (A), (B) plus (C) in the total amount of the surfactants in the composition is 30% by weight or greater when the composition is a solid form, 20% by weight or greater when the composition is a paste form, and 5% by weight or greater when the composition is a liquid form. It is desirable that the pH of the detergent composition of the present invention be adjusted to 2 to 10, particularly 4 to 8, using acid or alkaline agents known in the art.

Other features of the invention will become apparent in the course of the following description of the exemplary embodiments which are given for illustration of the invention and are not intended to be limiting thereof.

EXAMPLES

Example 1

Shampoos having formulations listed in Table 1 were prepared according to a conventional method. Feeling of foam was evaluated for each detergent composition. The results are presented in Table 1.

Evaluation Method (1) Feeling of the foam to the hair 20 g of a tress of human hair was moistened with water at 40° C. to contain 15 g of water. The tress was washed with one (1) gm of a detergent composition. Then, the feeling of the foam was sensuously evaluated by 10 panelists of expert women.

(2) Feeling of the foam to the skin

One (1) gm of a detergent composition was taken in the hand which had been moistened with water at 40° C. After foaming the detergent and washing the hand, the feeling of the foam was sensuously evaluated by 10 panelists of expert women.

| | <Evaluation standard> |
|---|---|
| AAA: | More slippery than the standard composition or the appearance of the foam is creamy |
| BBB: | Same as or worse than the standard composition |
| <Standard Composition> | |
| Decylpolyglucoside ($R_1 = C_{10}$, m = 0, G = Glucose residue, n = 1.3 in formula (I)) | 15% by weight |
| Lauryl sulfate triethanol amine | 5% |
| Perfume, Water | Balance |
| Total | 100 |

TABLE 1

| | (components: % by weight) | | | | | | | | | | |
|---|---|---|---|---|---|---|---|---|---|---|---|
| | Inventive Product | | | | | Comparative Product | | | | | |
| | 1 | 2 | 3 | 4 | 5 | 1 | 2 | 3 | 4 | 5 | 6 |
| Decylpolyglucoside *1 | 10 | 10 | 10 | 10 | | | | 10 | 10 | 10 | 10 |
| Dodecylpolyglucoside *2 | | | | | 10 | 10 | 10 | | | | |
| Sodium polyoxyethylene(3) lauryl sulfate | 7 | | | | 7 | 7 | 7 | 7 | | | |
| Sodium $C_{14}$-α-olefin sulfonate | | 7 | | | | | | | 7 | | |
| N-lauryl glutamate monotriethanol amine | | | 7 | | | | | | | 7 | |
| Mono-lauryl phosphate di-triethanol amine | | | | 7 | | | | | | | 7 |
| Sucrose fatty acid ester *3 | 3 | 3 | 3 | 3 | 3 | — | 0.05 | — | — | — | — |
| Perfume, Water | | | Balance | | | | | Balance | | | |
| Evaluation of foam | | | | | | | | | | | |

TABLE 1-continued

| | (components: % by weight) | | | | | | | | | | |
|---|---|---|---|---|---|---|---|---|---|---|---|
| | Inventive Product | | | | | Comparative Product | | | | | |
| | 1 | 2 | 3 | 4 | 5 | 1 | 2 | 3 | 4 | 5 | 6 |
| When washing the Hair | | | | | | | | | | | |
| Creaminess | AAA | AAA | AAA | AAA | AAA | BBB | BBB | BBB | BBB | BBB | BBB |
| Slipperiness | AAA | AAA | AAA | AAA | AAA | BBB | BBB | BBB | BBB | BBB | BBB |
| When washing the Skin | | | | | | | | | | | |
| Creaminess | AAA | AAA | AAA | AAA | AAA | BBB | BBB | BBB | BBB | BBB | BBB |
| Slipperiness | AAA | AAA | AAA | AAA | AAA | BBB | BBB | BBB | BBB | BBB | BBB |

*1 $R_1$: $C_{10}$, m: 0, G: glucose residue, n: 1.3 in formula (I)
*2 $R_1$: $C_{12}$, m: 0, G: glucose residue, n: 1.6 in formula (I)
*3 Fatty acid: Lauric acid, mono/di or tri: 7/3

Example 2

Detergent compositions shown below were prepared and the effect of various sucrose fatty acid esters was investigated. The results are shown in Table 2.

| | |
|---|---|
| Decylpolyglucoside ($R_1 = C_{10}$, m = o, G = Glucose residue, n = 1.3 in formula (I)) | 15% by weight |
| Sucrose fatty acid ester (See TABLE 2) | 3% |
| Mono-lauryl phosphate di-triethanol amine | 10% |
| Perfume | Appropriate amount |
| Water | Balance |
| Total | 100 |

(Evaluation Standard)
AAA: Excellent
BBB: Good
CCC: Normal

TABLE 2

| Sucrose fatty acid ester | | Feeling of Foam | |
|---|---|---|---|
| Fatty acid | Proportion of mono/di or tri | Slipperiness | Creaminess |
| Lauric acid | 100/0 | BBB | BBB |
| Lauric acid | 60/40 | AAA | AAA |
| Lauric acid | 30/70 | AAA | AAA |
| Lauric acid | 0/100 | BBB | BBB |
| Palmitic acid | 70/30 | AAA | AAA |
| Palmitic acid | 30/70 | AAA | AAA |
| Stearic acid | 60/40 | AAA | AAA |
| Eicosanic acid | 70/30 | AAA | AAA |
| Behenic acid | 50/50 | AAA | AAA |

Example 3

A shampoo having the formulation shown below was prepared. The shampoo yielded creamy foam and rendered an excellent feel after washing.

| | |
|---|---|
| Decylpolyglucoside ($R_1 = C_{12}$, m = 0, G = Glucose residue, n = 3.0 in formula (I)) | 10% by weight |
| Disodium polyoxyethylene(3) lauryl sulfosuccinate | 5% |
| Sucrose fatty acid ester *4 | 3% |
| Perfume | 0.3% |
| Water | Balance |
| Total | 100 |

*4: DK ester S-L18A (Manufactured by Daiichi Kogyo Seiyaku Co., Ltd.)

Example 4

A body shampoo having the formulation shown below was prepared. The body shampoo yielded creamy foam and was less-irritant to the skin.

| | |
|---|---|
| Polyoxyethylene(3) lauryl glucoside (n: 1.5) | 10% by weight |
| Sodium laurate | 10% |
| Sucrose fatty acid ester *5 | 5% |
| Ethylene glycol distearate | 3% |
| Perfume | 0.6% |
| Water | Balance |
| Total | 100 |

*5: DK ester S-L18A (Manufactured by Daiichi KogyoSeiyaku Co., Ltd.)

The detergent compositions of the present invention are capable of producing creamy and sufficient lather which is not irritant to the skin. The detergent compositions are particularly suitable for use as shampoos and body shampoos.

Obviously, numerous modifications and variations of the present invention are possible in light of the above teachings. It is therefore to be understood that within the scope of the appended claims, the invention may be practiced otherwise than as specifically described herein.

What is claimed is:

1. An aqueous shampoo composition, consisting essentially of
   (A) 1 to 40% by weight of an alkyl saccharide surfactant represented by the formula (I)

$$R_1O\text{—}(R_2O)_m\text{—}(G)_n \qquad (I)$$

wherein $R_1$ represents a linear or branched alkyl, alkenyl, or alkyl phenyl group having $C_{6-18}$ carbon atoms, $R_2$ represents an alkylene group having $C_{2-4}$ carbon atoms, G represents a reducing sugar having a $C_{5-6}$ carbon atom content, m denotes a value 0 to 10, and n denotes a value of 1 to 10;
   (B) 0.3–10% by weight of a sucrose fatty acid ester represented by the formula (II)

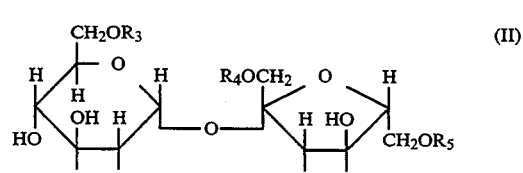

(II)

wherein $R_3$, $R_4$, and $R_5$, which may be the same or different, represents a linear or branched, saturated or unsaturated acyl group having a $C_{8-24}$ carbon atom content or a hydrogen atom, provided that at least one of $R_3$, $R_4$, or $R_5$ is an acyl group;
   (C) 5 to 20% by weight of at least one anionic surfactant, optionally, (D) a component selected from the group consisting of propylene glycol, glycerin, sorbitol, polyoxyethyleneglycol distearate, ethanol, trichlosan, trichlorocarban, potassium glycyrrhetinate, tocopherol acetate, zinc pyrithione, octopirox, methyl paraben, butyl paraben, perfumes, pigments and ultraviolet ray absorbers, (E) balance water.

2. The aqueous shampoo composition of claim 1 consisting essentially of water, 10 wt. % of said alkyl saccharide surfactant, 3 wt. % of said sucrose fatty acid ester and 7 wt. % of said anionic surfactant.

3. The aqueous shampoo composition of claim 1 consisting essentially of water and 10–15 wt. % of an alkyl saccharide surfactant represented by formula (I), 3–5 wt. % of a sucrose fatty acid ester of formula (II) and 5–10 wt. % of at least one anionic surfactant.

4. An aqueous shampoo composition consisting of water;

(A) 1 to 40% by weight of an alkyl saccharide surfactant represented by the formula (I)

wherein $R_1$ represents a linear or branched alkyl, alkenyl, or alkylphenyl group having $C_{6-18}$ carbon atoms, $R_2$ represents an alkylene group having $C_{2-4}$ carbon atoms, G represents a reducing sugar having a $C_{5-6}$ carbon atoms content, m denotes a value of 0 to 10, and n denotes a value of 1 to 10;

(B) 0.3 to 10% by weight of a sucrose fatty acid ester represented by the formula (II)

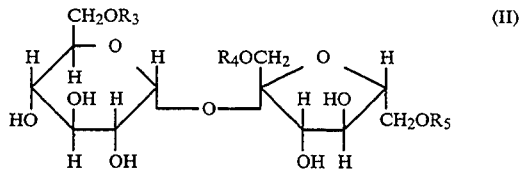

wherein $R_3$, $R_4$, and $R_5$, which may be the same or different, represents a linear or branched, saturated or unsaturated acyl group having a $C_{8-24}$ carbon atom content or a hydrogen atom, provided that at least one of $R_3$, $R_4$, or $R_5$ is the acyl group; and (C) 5 to 20% by weight of at least one anionic surfactant.

5. The aqueous shampoo composition of claim 4 consisting of 10–15 wt. % of an alkyl saccharide surfactant represented by formula (I), 3–5 wt. % of a sucrose fatty acid ester of formula (II) and 5–10 wt. % of at least one anionic surfactant.

6. The aqueous shampoo composition as claimed in claim 4 further consisting of at least one material selected from the group consisting of humectants, biocidal agents, antiphlogistic agents, anti-dandruff agents, antiseptics, pearlescent agents, perfumes, pigments, ultraviolet ray absorbers and antioxidants.

7. The aqueous shampoo composition as claimed in claim 6 wherein said humectants are selected from the group consisting of propylene glycol, glycerin and sorbitol, said biocidal agents are selected from the group consisting of Trichlosan, and Trichlorocarban, said antiphlogistic agents are selected from the group consisting of potassium glycyrrhetinate and tocopherol acetate, said anti-dandruff agents are selected from the group consisting of zinc pyrithione and octopirox, and said antiseptics are selected from the group consisting of methyl paraben and butyl paraben.

8. The aqueous shampoo composition as claimed in claim 4, further consisting of perfume.

* * * * *